(12) United States Patent
Ashu

(10) Patent No.: US 10,366,598 B1
(45) Date of Patent: Jul. 30, 2019

(54) COMBINATION AIR FRESHENER AND SECURITY ALARM

(71) Applicant: Wilson Ekanyie Ashu, Fort Worth, TX (US)

(72) Inventor: Wilson Ekanyie Ashu, Fort Worth, TX (US)

(*) Notice: Subject to any disclaimer, the term of this patent is extended or adjusted under 35 U.S.C. 154(b) by 0 days.

(21) Appl. No.: 15/436,783

(22) Filed: Feb. 18, 2017

Related U.S. Application Data
(60) Provisional application No. 62/296,693, filed on Feb. 18, 2016.

(51) Int. Cl.
| | | |
|---|---|---|
| G08B 25/10 | (2006.01) | |
| B05B 11/00 | (2006.01) | |
| A61L 9/14 | (2006.01) | |
| A61L 9/12 | (2006.01) | |

(52) U.S. Cl.
CPC ............ G08B 25/10 (2013.01); A61L 9/14 (2013.01); B05B 11/3081 (2013.01); A61L 9/12 (2013.01); A61L 2209/11 (2013.01); A61L 2209/111 (2013.01)

(58) Field of Classification Search
CPC ... G08B 25/10; A61L 9/14; A61L 9/12; A61L 2209/11; A61L 2209/111; B05B 11/3081
USPC .............. 239/67–73, 281, 337; 340/540–541
See application file for complete search history.

(56) References Cited

U.S. PATENT DOCUMENTS

| | | | | |
|---|---|---|---|---|
| 4,415,797 A * | 11/1983 | Choustoulakis | ..... | A01M 1/2038 222/644 |
| 4,495,560 A * | 1/1985 | Sugimoto | .......... | B60H 1/00814 700/34 |
| 5,055,822 A * | 10/1991 | Campbell | ................ | G08B 1/00 116/214 |
| 5,958,346 A * | 9/1999 | Evans, Jr. | ................. | A61L 9/12 239/44 |
| 6,454,185 B2 * | 9/2002 | Fuchs | ............... | A61M 15/0065 239/316 |
| 6,881,382 B2 * | 4/2005 | Goldstein | ................ | A61L 9/03 116/200 |
| 7,089,780 B2 * | 8/2006 | Sunshine | ............. | G01N 29/022 340/541 |
| 8,074,640 B2 * | 12/2011 | Davies | ................ | A01M 1/2044 128/200.14 |
| 8,269,640 B2 * | 9/2012 | Ueno | ..................... | G08B 15/02 340/520 |
| 8,881,945 B2 * | 11/2014 | Gasper | ................ | A01M 1/2038 222/1 |
| 9,082,274 B2 * | 7/2015 | Goto | ........................ | G08B 1/00 |
| 9,649,400 B2 * | 5/2017 | Furner | ................ | A01M 7/0003 |
| 2003/0038718 A1 * | 2/2003 | Clauss | .................. | A62C 37/40 340/521 |
| 2006/0261967 A1 * | 11/2006 | Marman | .............. | G08B 17/103 340/630 |

(Continued)

Primary Examiner — Steven J Ganey
Assistant Examiner — Joseph A Greenlund
(74) Attorney, Agent, or Firm — Kenneth L. Tolar

(57) ABSTRACT

A combination air freshener and security alarm includes a housing having a touch-screen display that programs and controls a plurality of sensors, a cellular-transmission module and a fragrance-dispersal mechanism. Therefore, a user can designate which of a plurality of desired fragrances will be dispersed at select intervals. In addition, if the sensors detect any unusual noise, airborne contaminants, excessive heat or motion in the surrounding area, a distress signal is wirelessly transmitted to a remote electronic device.

10 Claims, 2 Drawing Sheets

(56) References Cited

U.S. PATENT DOCUMENTS

| | | | |
|---|---|---|---|
| 2006/0290522 A1* | 12/2006 | Tajima | G08B 1/08 |
| | | | 340/577 |
| 2007/0095941 A1* | 5/2007 | Gorres | A01M 1/2044 |
| | | | 239/337 |
| 2010/0117828 A1* | 5/2010 | Goldman | G08B 7/06 |
| | | | 340/540 |
| 2010/0237108 A1* | 9/2010 | Anderson | B65D 83/262 |
| | | | 222/646 |
| 2011/0181410 A1* | 7/2011 | Levinson | G06F 19/3456 |
| | | | 340/540 |
| 2013/0068788 A1* | 3/2013 | Gasper | A01M 1/2038 |
| | | | 222/63 |
| 2015/0328355 A1* | 11/2015 | Rubin | F24F 3/1603 |
| | | | 422/4 |

\* cited by examiner

COMBINATION AIR FRESHENER AND SECURITY ALARM

CROSS REFERENCE TO RELATED APPLICATIONS

This application is entitled to the benefit of provisional patent application number 62/296,693 on Feb. 18, 2016, the specification of which is incorporated herein by reference.

BACKGROUND OF THE INVENTION

The present invention relates to an electronic fragrance dispenser having incorporated sensors for surreptitiously initiating an emergency response when an alarm condition is detected.

DESCRIPTION OF THE PRIOR ART

Most homeowners separately procure various home-protection devices, such as smoke, fire, burglar and flood alarms, and sometimes temperature sensors. Installing and maintaining a multitude of such devices is burdensome, laborious and irritating. Furthermore, the response mechanisms of the devices vary tremendously and are often unreliable or ineffective. Many also require separate monitoring-service contracts, which are costly and an organizational nightmare.

Accordingly, there is currently a need for a device that overcomes the disadvantages of installing, maintaining and monitoring multiple home-protection sensors. The present invention addresses this need by providing an air freshener that monitors various ambient parameters, such as motion, extreme temperature variations, smoke intrusion or excessive noise, and surreptitiously initiates an emergency response if an alarm condition is detected.

SUMMARY OF THE INVENTION

The present invention relates to a combination air freshener and security alarm comprising a housing having a touch-screen display that programs and controls a plurality of sensors, a cellular-transmission module and a fragrance-dispersal mechanism. Therefore, a user can designate which of a plurality of desired fragrances will be dispersed at select intervals. In addition, if the sensors detect any unusual noise, airborne contaminants, heat or motion in the surrounding area, a distress signal is wirelessly transmitted to a remote electronic device.

It is therefore an object of the present invention to provide an automated air freshener that also monitors ambient conditions within a building.

It is therefore another object of the present invention to provide an air freshener that eliminates the burden associated with installing, maintaining and monitoring multiple home-protection sensors.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
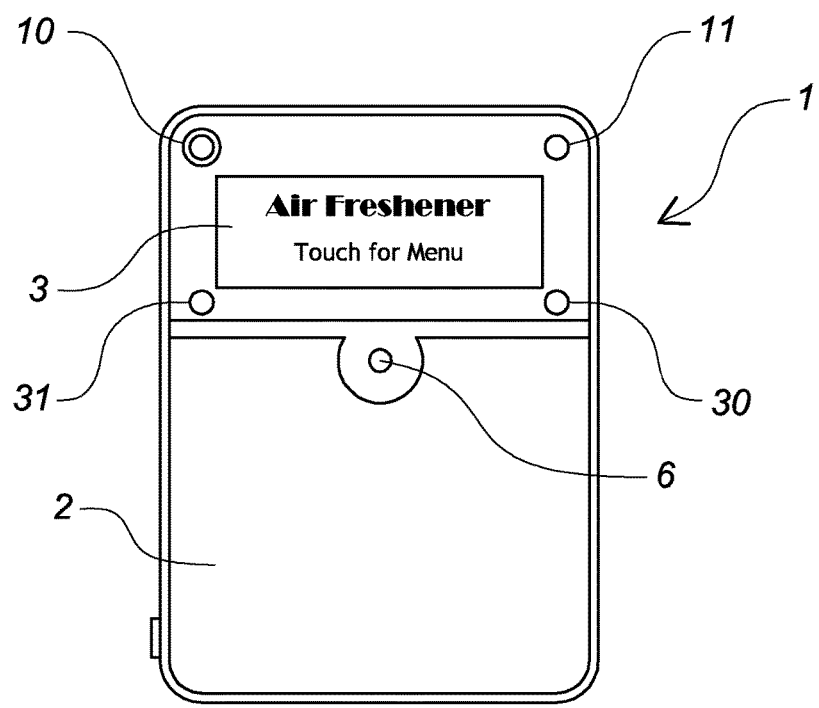
FIG. 1 is a front, plan view of the air freshener according to present invention.
Figure 2:
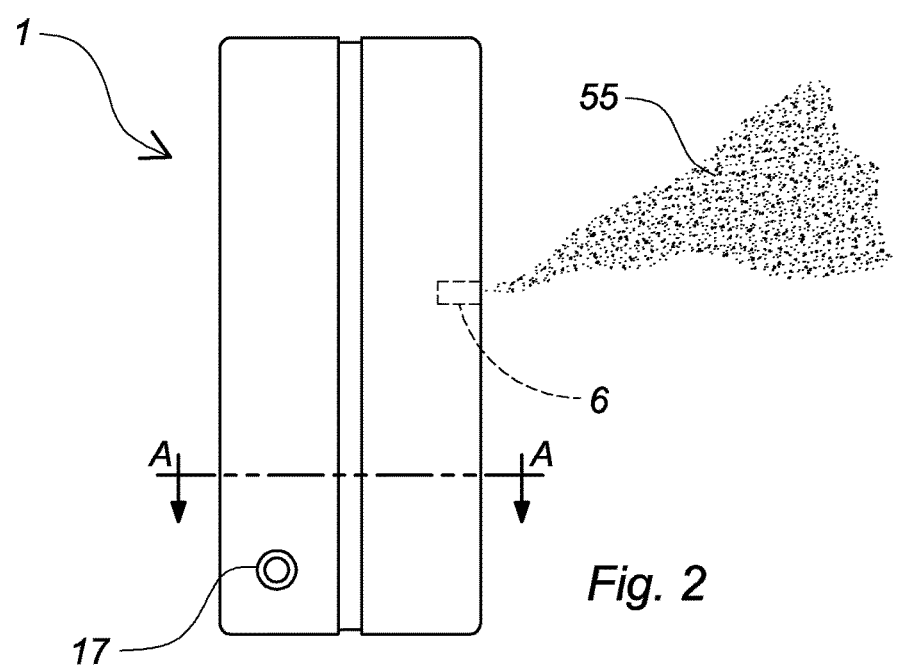
FIG. 2 is a side view of the air freshener.
Figure 3:
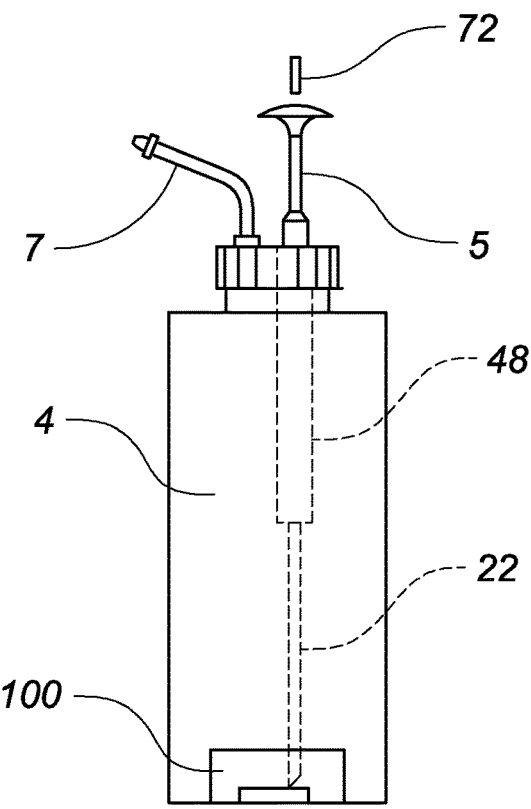
FIG. 3 is an isolated, enlarged view of an exemplary deodorizing-liquid reservoir.
Figure 4:
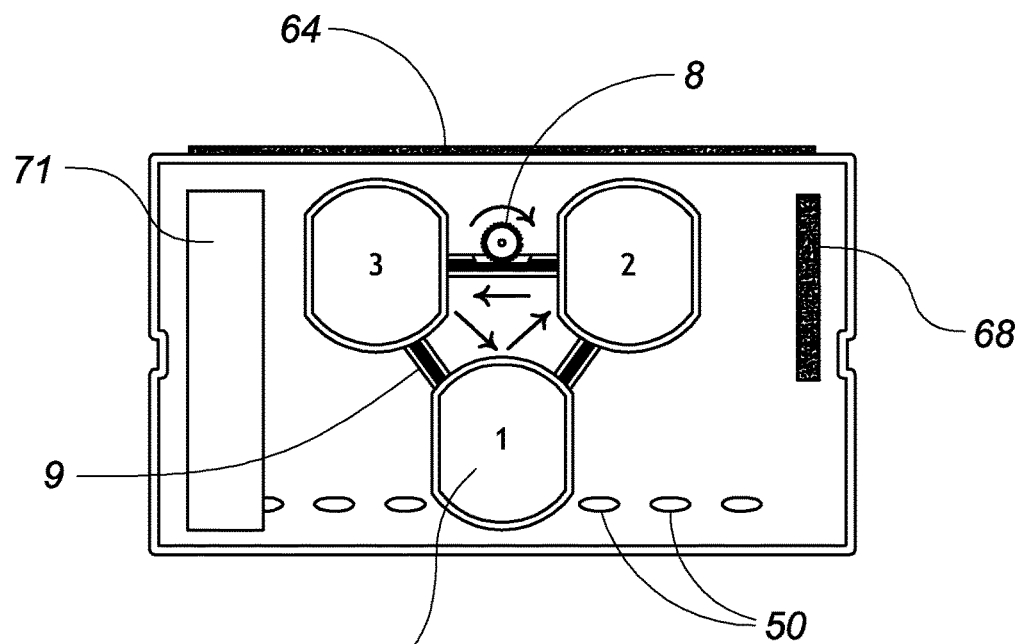
FIG. 4 is a top, sectional view of the housing taken along A-A in FIG. 2, depicting the internal reservoirs and associated track mechanism.

The present invention relates to a combination air freshener and security alarm comprising a housing 1 having a front surface 2, a plurality of peripheral walls and an interior chamber. The rear surface includes an adhesive layer 64 for mounting the housing on a wall or other support surface. On the front surface is a touch-screen display 3 in communication with a microprocessor and associated operating system for programming and controlling a plurality of sensors, a cellular-transmission module and a fragrance-dispersal mechanism, as described below. The processor and cellular transmission module are mounted on a printed circuit board 68 within the interior chamber.

Also received within the interior chamber are a plurality of reservoirs 4, each containing a deodorizing liquid 55 having a discrete fragrance to allow a user to designate a particular fragrance to be dispersed at desired intervals. Each reservoir includes a manual pump 48 having a spring-biased, depressible plunger 5 connected to a suction tube 22 that disperses a predetermined amount of the deodorizing liquid through a discharge port 6 on the housing front surface. Upon receiving a command from the microprocessor, an adjacent solenoid pin 72 depresses the plunger to expel the liquid through a nozzle 7 that has been aligned with the discharge port 6. The pin subsequently retracts and releases the plunger to intake a predetermined amount of the liquid into the suction tube for a subsequent dispersal.

Each reservoir includes an optical fluid level sensor that wirelessly transmits a message to the remote electronic device when the liquid level falls below a predetermined threshold. A DC gear motor, associated linkage mechanism 8 and a conveyor move the reservoirs along a guide track 9 to align the nozzle 7 on a select reservoir with the discharge port 6, and position the plunger in proper relation to the solenoid pin, to dispense the desired fragrance. The lower surface of each reservoir includes a keyed indention 100 that mates with a carrier on the conveyor. Therefore, a user can remove, refill and replace the reservoirs as desired.

The internal cellular module transmits various alert messages to a remote smart phone or another electronic device if an alarm condition is detected. Adjacent to the display is a microphone 31 that detects abnormal ambient noises, such as glass breakage, causing the transmission module to surreptitiously transmit an alert notification to the remote device. Likewise, a motion detector 30 senses movement of large heat sources and activates a camera 10 to record still or video images that are wirelessly transmitted to the remote device. All of the internal electronic and mechanical components are powered with a rechargeable battery 71, which may be replenished with a power cord connected to a charging port 17, or a solar-powered fan within the housing.

When the device is first installed, the camera is programmed to photograph the surrounding area and to store the image in a database or on a removable SD card for comparison with subsequent photographs of the same area, which have been taken at random intervals. Therefore, any appreciable change in the captured images could indicate a disastrous event, such as a flood or earthquake, which will trigger an emergency transmission to the remote device.

An LED 11 on the front surface of the housing illuminates the surrounding area to enhance the quality of any recorded images. Furthermore, the LED transmits a light beam to a reflector positioned on an opposing wall to detect unusual air opacity that could indicate the presence of an airborne contaminant, such as smoke or dust. If the opacity is above a predefined level, a distress signal is wirelessly transmitted to the portable electronic device. On the lower surface of the housing are a plurality of weep holes 50 that allow ambient air intrusion to cool the internal electronics and to allow any accumulated moisture to drain from the interior.

Accordingly, the device periodically emits one or more select fragrances at desired intervals to deodorize the surrounding area. If any of the sensors detect an unusual condition, an alarm message and any recorded images are transmitted to the remote device to allow a supervisor to immediately implement corrective action.

The above-described device is not limited to the exact details of construction and enumeration of parts provided herein. For example, the device could also include metal detectors for identifying weapons, or other sensors for detecting dangerous non-metallic objects, such as powderous explosives or plastic, as with airport detectors. The camera could be programmed to capture images of the individuals carrying detected weapons or powder for later review and retrieval. The system could also be integrated with an airplane to record events during a given flight to assist with preventing or investigating certain occurrences, such as a hijacking. The system may also include a voice-activated or remote actuator for manually triggering the transmission of an alarm message. In addition, the system could communicate with a long-distance motion sensor for receiving and relaying indications that suspicious activity is occurring at remote locations. Furthermore, the size, shape and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A combination air freshener and security alarm comprising:
   a housing having an exterior surface and an interior chamber;
   a plurality of reservoirs within the interior chamber, each of said reservoirs containing a deodorizing liquid having a discrete fragrance;
   a pump with a designated actuating plunger mounted on each of said reservoirs that, when depressed, disperses a predetermined amount of the deodorizing liquid through a nozzle;
   a solenoid pin adjacent to said plunger that depresses and releases said plunger upon receipt of a predetermined command to deliver the liquid through the nozzle;
   means for moving each of said reservoirs to align the nozzle on the select one of said reservoirs with a discharge port on the exterior surface of said housing, wherein said means for moving each of said reservoirs includes a motor; a linkage driven by said motor, and a conveyor that moves the reservoirs along a guide track to align the nozzle on the select reservoir with the discharge port, and to position the plunger adjacent to said solenoid pin to dispense the desired fragrance;
   at least one atmospheric sensor on the exterior surface of said housing for monitoring a predetermined parameter;
   means for automatically transmitting a wireless distress signal to a remote electronic device in the event said sensor determines the predetermined parameter is outside a predefined range.

2. The combination according to claim 1 wherein said means for wirelessly transmitting a distress signal to a remote electronic device comprises:
   a wireless telephone transmitter;
   a controller in communication with said sensor and said wireless telephone transmitter, said controller instructing said wireless telephone transmitter to transmit the distress signal when the parameter is outside the predefined range.

3. The combination according to claim 1 wherein said sensor is a microphone that detects ambient noise.

4. The combination according to claim 1 wherein said sensor is a motion detector.

5. The combination according to claim 1 wherein said sensor is an ambient-air opacity detector for detecting airborne particles.

6. The combination according to claim 5 wherein said ambient-air opacity detector comprises:
   a reflector positioned within the surrounding area;
   a light on the exterior surface of said housing for projecting a light beam toward said reflector.

7. The combination according to claim 1 wherein said sensor is a temperature sensor.

8. The combination according to claim 1 further comprising a camera on the exterior surface of said housing for recording images of a surrounding area.

9. The combination according to claim 8 further comprising:
   means for actuating said camera to record at least two images at spaced intervals;
   means for comparing a first of said two images with a second of said two images;
   means for transmitting a distress signal to the remote electronic device if said first of said two images differs from the second of said two images.

10. The combination according to claim 1 wherein said sensor is selected from the group consisting of:
    a microphone that detects ambient noise;
    a motion detector;
    an ambient-air opacity detector for detecting airborne particles; and
    a temperature sensor.

* * * * *